(12) United States Patent
Ruano et al.

(10) Patent No.: US 8,476,012 B2
(45) Date of Patent: Jul. 2, 2013

(54) PHYSIOGENOMIC METHOD FOR PREDICTING METABOLIC AND CARDIOVASCULAR SIDE EFFECTS OF THIAZOLIDINEDIONES

(75) Inventors: Gualberto Ruano, Milford, CT (US); Andreas Windemuth, S. Glastonbury, CT (US); Steven D. Hanks, Farmington, CT (US)

(73) Assignee: Genomas, Inc., Hartford, CT (US)

( * ) Notice: Subject to any disclaimer, the term of this patent is extended or adjusted under 35 U.S.C. 154(b) by 939 days.

(21) Appl. No.: 12/424,725

(22) Filed: Apr. 16, 2009

(65) Prior Publication Data

US 2009/0263814 A1 Oct. 22, 2009

Related U.S. Application Data

(60) Provisional application No. 61/046,110, filed on Apr. 18, 2008.

(51) Int. Cl.
*C12Q 1/68* (2006.01)
*C12P 19/34* (2006.01)
*C07H 21/02* (2006.01)
*C07H 21/04* (2006.01)

(52) U.S. Cl.
USPC .......... 435/6.1; 435/91.1; 536/23.1; 536/24.3

(58) Field of Classification Search
None
See application file for complete search history.

(56) References Cited

U.S. PATENT DOCUMENTS

2006/0234262 A1 10/2006 Ruano et al.
2006/0278241 A1 12/2006 Ruano
Lucentini (The Scientist; 2004, vol. 24, p. 20).*

OTHER PUBLICATIONS

Hegele (Arterioscler. Thromb. Vasc. Biol.; 2002, vol. 22, pp. 1058-1061).*
Langdahl (Journal of Bone and Mineral Research 2000 vol. 15, No. 3, pp. 402-414).*
Wall (Nature Reviews Genetics (2003) vol. 4, pp. 587-597).*
dbSNP Short Genetic Variations; Quiry Result Showing Merger No.; 1 page; http://www.ncbi.nlm.nih.gov/snp/?term=rs6586179+& SITE=NcbiHome&submit=Go; printed Jun. 1, 2012.
dbSNP Short Genetic Variations; Reference SNP9refSNP) Cluster Report: rs903361; 5 pages; http://www.ncbi.nlm.nih.gov/projects/SNP/snp_ref.cgi?rs=903361; printed Jun. 1, 2012.
Kitts et al., "Chapter 5: the Single Nucleotide Polymorphism Database (dbSNP) of Nucleotide Sequence Variation"; In: McEntyre J, Ostell J, editors. The NCBI Handbook [Internet]. Bethesda (MD): National Center for Biotechnology Information (US); pp. 1-29; Oct. 9, 2002 [Updated Feb. 2, 2011].
dbSNP Short Genetic Variations; Reference Snp(refSNP) Cluster Report: rs1051339; 6 pages; http://www.ncbi.nlm.nih.gov/projects/SNP/snp_ref.cgi?rs=1051339; printed Jun. 1, 2012.

* cited by examiner

*Primary Examiner* — Jehanne Sitton
(74) *Attorney, Agent, or Firm* — Cantor Colburn LLP

(57) ABSTRACT

Disclosed herein are genetic markers related to the efficacy and/or safety of thiazolidinedione therapy identified by a physiogenomic methodology that correlates the genetic markers with a physiological response. The genetic markers described herein were not previously associated with the efficacy and/or safety of thiazolidinedione therapy. The markers related to safety are those associated with the important side effects of BMI increase and development of edema. In one embodiment, markers related to efficacy of thiazolidinedione therapy are associated with glycosylated hemoglobin. Method of assessing an individual for markers associated with the safety and/or efficacy of thiazolidinedione therapy are described.

7 Claims, 6 Drawing Sheets

PHYSIOGENOMIC METHOD FOR PREDICTING METABOLIC AND CARDIOVASCULAR SIDE EFFECTS OF THIAZOLIDINEDIONES

CROSS-REFERENCE TO RELATED APPLICATIONS

This application is a Nonprovisional of U.S. Provisional Application No. 61/046,110, filed Apr. 18, 2008, which is incorporated by reference herein in their entirety.

BACKGROUND

Thiazolidinediones, TZDs (also known as glitazones) reverse insulin resistance in type 2 diabetes and potentially offer comprehensive treatment of the disease. Black box warnings on the labels of rosiglitazone (Avandia®) and pioglitazone (Actos®), the two currently marketed drugs in the class, were required by the FDA in August 2007 to alert the medical community to a risk heart failure. In accordance with the required warning, patients should be observed carefully for signs and symptoms of heart failure, including excessive, rapid weight gain, dyspnea, and/or edema. Furthermore, the thiazolidinediones are contraindicated in advanced congestive heart failure.

Currently, the development of thiazolidinedione side effects is unpredictable and potentially injurious to the patient, which discourages patient compliance and disrupts healthcare delivery. Such uncertainties burden medical management and increase healthcare costs. Much of the mechanistic insight into the metabolic and cardiovascular side effects of these drugs has been learned from animal studies. There is an urgent need to garner scientific evidence from human clinical studies to prioritize the use of thiazolidinediones.

Thiazolidinedione therapy induces a mean weight gain of 4 to 5 kg, and doubles or triples the risk of edema. Weight gain exacerbates the diabetic condition itself and may be the result of adiposity, fluid retention, or a combination of the two. Peroxisome proliferator-activated receptor (PPARG) agonists such as the thiazolidinediones contribute to adiposity through adipogenesis and increased fat accretion. Microcirculatory dysregulation and vascular permeability are already present in diabetes. PPAR gamma type receptor agonists as a class may promote edema through fluid retention due to renal sodium reabsorption and increased adipose tissue vascular permeability. Effects may also be drug specific.

Physiogenomics is a medical application of sensitivity analysis and systems engineering that defines a new paradigm in the genetic analysis of complex human phenotypes. Sensitivity analysis is the study of the dependence of a system on changes in its components. In physiogenomics, single nucleotide polymorphisms (SNPs), for example, provide the variable components of genes, and analysis of the relationship between that variation and the physiological response provides information about which genes play important roles in the physiological process. This approach has been advanced in human clinical studies and in animal models. The associated gene markers are combined into SNP ensembles harnessing their combined predictive power to estimate functional variability among individuals similarly treated.

By testing broad hypotheses about mechanistic features of drug effects, physiogenomics can generate novel hypotheses in relation to mechanisms of drug safety. Needed are improvements in the understanding of the weight and edema profiles of patients treated with rosiglitazone or pioglitazone.

SUMMARY

In one embodiment, a physiogenomics method for determining a human individual's protection from or risk for developing one or more adverse side effects associated with the use of a thiazolidinedione drug comprises assaying genetic material from the human individual for the presence of a risk genetic marker and a protective genetic marker to produce a combinatorial genotype for the human individual, wherein the adverse side effect is associated with increased body mass index, increased edema, or a combination thereof, and determining the protection from or risk for developing the one or more adverse side effects in the human individual in response the use of a thiazolidinedione drug by comparing the combinatorial genotype for the human individual with a predictive model comprising phenotype and genotype data for a thiazolidinedione drug-treated population.

In another embodiment, a physiogenomics method for determining a human individual's therapeutic effect from the use of a thiazolidinedione drug comprises assaying genetic material from the human individual for the presence of a risk genetic marker and a protective genetic marker to produce a combinatorial genotype for the human individual, wherein the risk marker is associated with a lack of therapeutic effectiveness of thiazolidinedione therapy measured as HbA1C level and the protective marker is associated with a positive therapeutic effect of thiazolidinedione therapy measured as HbA1C level, and determining the human individual's therapeutic effect from the use of a thiazolidinedione drug by comparing the combinatorial genotype for the human individual with a predictive model comprising phenotype and genotype data for a thiazolidinedione drug-treated population.

In another embodiment, method of producing a combinatorial genotype for the safety and efficacy of thiazolidinedione therapy for a human individual comprises assessing the individual for the presence or absence of a first risk marker and a first protective marker to produce a side effect combinatorial genotype for the individual, wherein the adverse side effect is associated with increased body mass index or edema, and wherein the first risk marker is associated with an increased risk of developing the adverse side effect and the first protective marker is associated with a decreased risk of developing the adverse side effect. The method also includes assessing the individual for the presence or absence of a second risk marker and a second protective marker to produce a therapeutic effectiveness combinatorial genotype for the individual, wherein the second risk marker is associated with a lack of therapeutic effectiveness of thiazolidinedione therapy measured as HbA1C level and the second protective marker is associated with a positive therapeutic effect of thiazolidinedione therapy measured as HbA1C level. The side effect combinatorial genotype and the therapeutic effectiveness combinatorial genotype are combined to produce a combinatorial genotype for the safety and efficacy of thiazolidinedione therapy for the human individual.

The first panel shows the physiogenomics plot curve for SNP rs706713, which is located in the gene for PIK3R1. The frequency of the minor allele is 10% in subjects with good glucose control (left), and approaches 40% at the poor end of the response distribution (right).

Figure 3:
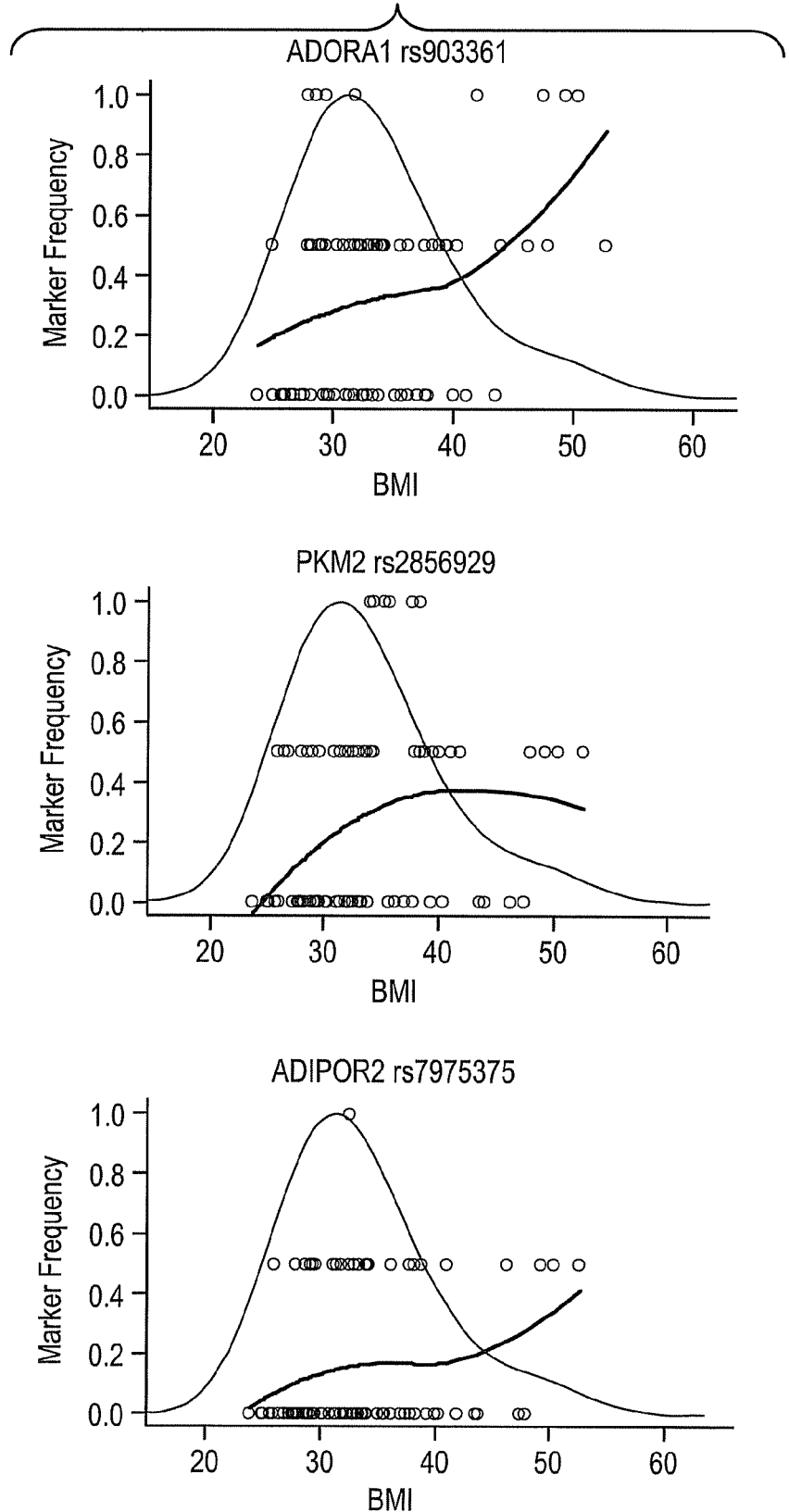

FIG. 3 shows individual genotypes (circles) of each SNP overlaid on the response distribution (thin line) for BMI.

Figure 4:
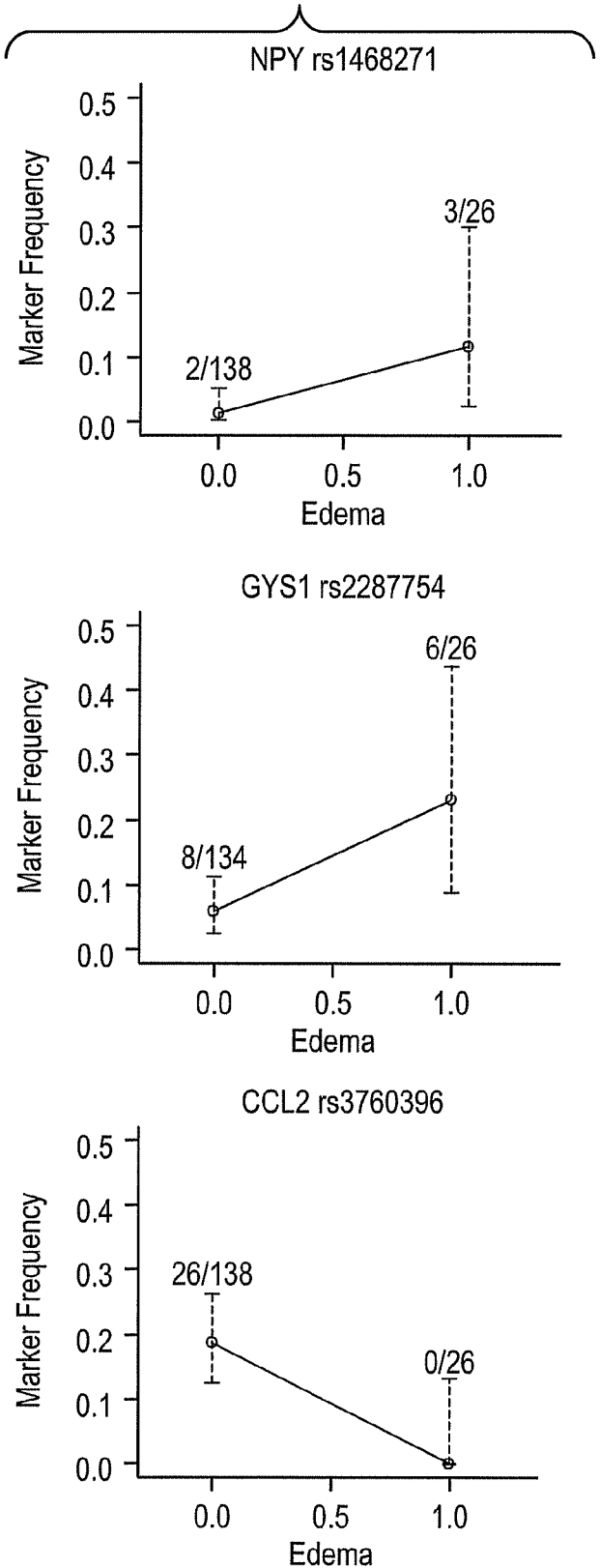

FIG. 4 shows individual genotypes (circles) of each SNP overlaid on the response distribution (thin line) for edema.

Figure 5:
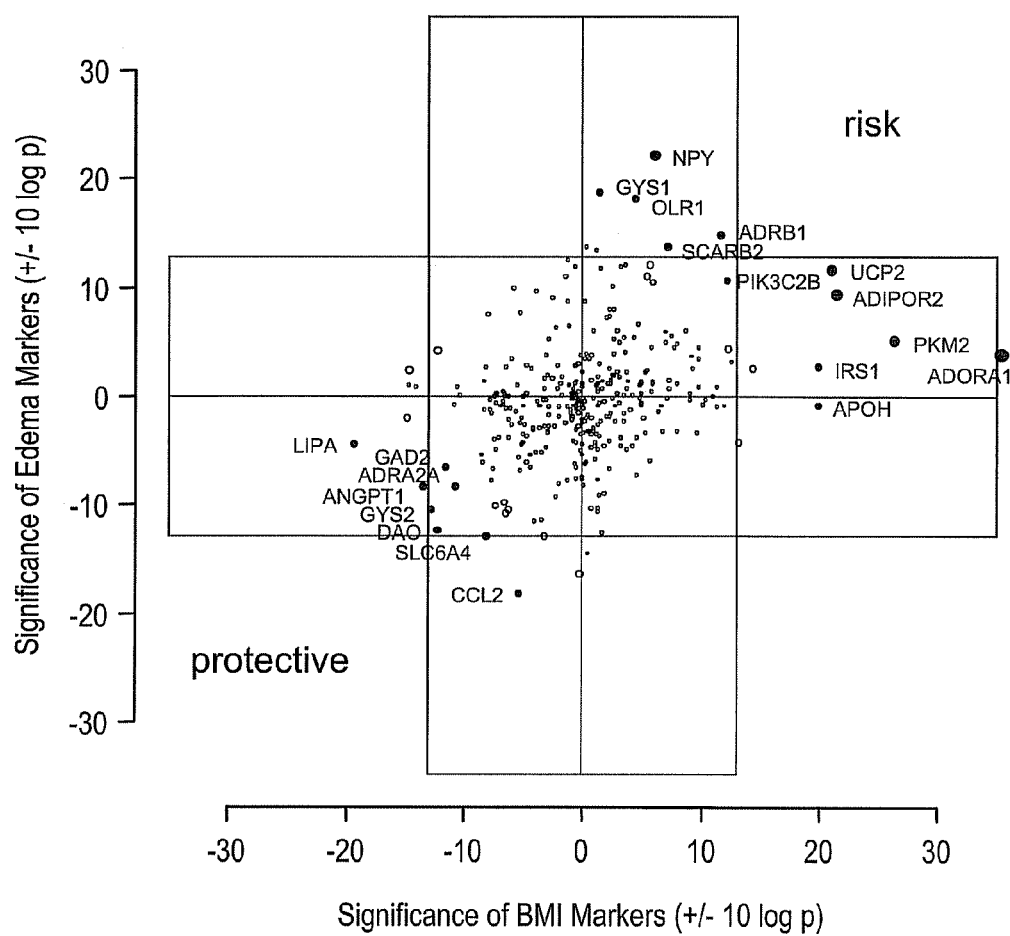

FIG. 5 shows physiogenomic contours of the associations for BMI and edema, showing risk markers on the upper right quadrant and protective markers on the lower left quadrant. Each axis represents a scale with scores that are ten times the absolute value of the log of the p value for the SNP association. The score was assigned a positive or negative value to correspond with the sign of the regression coefficient in Table 6. Sizes of data points are proportional to sum of the scores corresponding to both axes. Vertical and horizontal borders between shaded and unshaded sectors represent the unadjusted significance threshold $p<0.05$, or $\pm 13$ at $\pm(10\times|\log(0.05)|)$.

Figure 6:
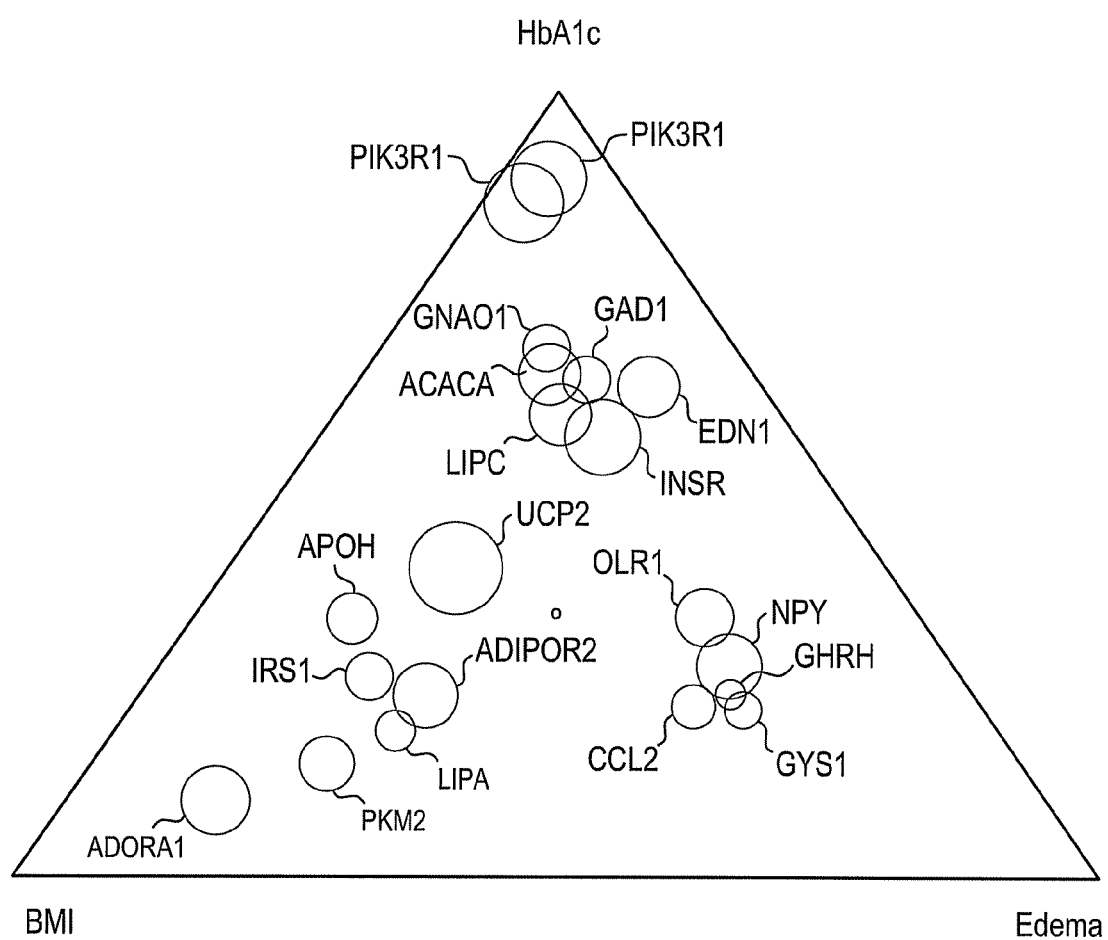

FIG. 6 is a physiogenomic contour showing overall degree of association (circle size) and relative degree of association between responses (circle position) for HbA1c, BMI and edema.

These and other embodiments, advantages and features of the present invention become clear when detailed description and examples are provided in subsequent sections.

DETAILED DESCRIPTION

Disclosed herein are genetic markers (e.g., variants) and sets of markers associated with the efficacy and/or safety of thiazolidinedione therapy identified by a physiogenomic methodology that correlates the genetic markers with a physiological response. A marker set associated with the efficacy and/or safety of thiazolidinedione therapy comprises a plurality of genetic variants in genes associated with BMI increase, the development of edema, or level of glycosylated hemoglobin. In one embodiment, the marker set comprises one risk marker and one protective marker associated with BMI increase, the development of edema, or level of glycosylated hemoglobin. A combinatorial genotype is produced by assaying the genetic material of the individual for the presence of a risk marker and a protective marker. The genetic markers described herein were not previously associated with the efficacy and/or safety of thiazolidinedione therapy. The markers related to safety are those associated with the important side effects of BMI increase and development of edema. In one embodiment, markers related to efficacy of thiazolidinedione therapy are associated with the level of glycosylated hemoglobin.

Also disclosed herein are methods of using the disclosed genetic markers to assess an individual for the efficacy and/or safety of thiazolidinedione therapy. The methods are useful for patients undergoing thiazolidinedione therapy as well as those for whom thiazolidinedione therapy may be indicated. In one embodiment, provided herein is a method of identifying an individual's phenotype of risk of BMI increase in response to thiazolidinedione therapy by determining a genotype newly identified as associated with BMI increase related to thiazolidinedione therapy. The method includes assaying genetic material from the individual for the presence of at least one risk marker and at least one protective marker to produce a combinatorial genotype for the individual. The at least one risk marker is associated with a risk of BMI increase and in response to thiazolidinedione therapy in the individual and, the at least one protective marker is not associated with a risk of BMI increase (e.g., protection) in response to thiazolidinedione therapy in the individual. The method includes determining the risk of BMI increase in the human individual in response the use of a thiazolidinedione drug by comparing the combinatorial genotype for the human individual with a predictive model comprising phenotype and genotype data for a thiazolidinedione drug-treated population.

In another embodiment, provided herein is a method of identifying an individual's phenotype of risk of edema in response to thiazolidinedione therapy by determining a genotype newly identified as associated with edema related to thiazolidinedione therapy. The method includes assessing the individual for the presence or absence of at least one risk marker and at least one protective marker to produce a combinatorial genotype for the individual. The at least one risk marker is associated with a risk of edema in response to thiazolidinedione therapy in the individual and the at least one protective marker is not associated with a risk of edema (e.g., protection) in response to thiazolidinedione therapy in the individual. The method includes correlating determining the risk of edema in the human individual in response the use of a thiazolidinedione drug by comparing the combinatorial genotype for the human individual with a predictive model comprising phenotype and genotype data for a thiazolidinedione drug-treated population.

In yet another embodiment, included is a method of identifying both a risk of BMI increase and a risk of edema associated with the physiological response to thiazolidinedione therapy in an individual.

In another embodiment, provided herein is a method of identifying an individual's phenotype of efficacy of thiazolidinedione therapy by determining a genotype newly identified as associated with the level of glycosylated hemoglobin in response to thiazolidinedione therapy. The method includes assessing the individual for the presence or absence of at least one risk marker and at least one protective marker to produce a combinatorial genotype for the individual. The at least one risk marker is associated with a lack of therapeutic effect and the at least one protective marker is associated with a positive therapeutic effect. The method includes determining the therapeutic effect of thiazolidinedione therapy in the human individual in response the use of a thiazolidinedione drug by comparing the combinatorial genotype for the human individual with a predictive model comprising phenotype and genotype data for a thiazolidinedione drug-treated population. In another embodiment, a method of producing a combinatorial genotype for the safety and efficacy of thiazolidinedione therapy for a human individual comprises assessing the individual for the presence or absence of a first risk marker and a first protective marker to produce a side effect combinatorial genotype for the individual, wherein the adverse side effect is associated with increased body mass index or edema, and wherein the first risk marker is associated with an increased risk of developing the adverse side effect and the first protective marker is associated with a decreased risk of developing the adverse side effect; assessing the individual for the presence or absence of a second risk marker and a second protective marker to produce a therapeutic effectiveness combinatorial genotype for the individual, wherein the second risk marker is associated with a lack of therapeutic effectiveness of thiazolidinedione therapy measured as HbA1C level and the second protective marker is associated with a positive therapeutic effect of thiazolidinedione therapy measured as HbA1C level; and combining the side effect combinatorial genotype and the therapeutic effectiveness combinatorial genotype to produce a combinatorial genotype for the safety and efficacy of thiazolidinedione therapy for the human individual. In one embodiment, thiazolidinedione therapy effectiveness is measured as a level of glycosylated hemoglobin.

The manifestation of adverse effects in patients receiving thiazolidinediones (e.g., rosiglitazone therapy), for example, is unpredictable from clinical presentation alone. The inventors herein have searched for ways to avoid the adverse effects of thiazolidinedione therapy based on individual gene variation. The inventors explored physiogenomic relationships between the thiazolidinedione effects deduced from BMI and edema profiles and an array of 384 SNP variations in 222 genes chosen to represent a variety of physiological pathways. 15 SNPs associated with the BMI profiles at $p \leq 0.05$, and 10 SNPs associated with edema at $p \leq 0.05$ were discovered. Advantageously, the SNPs associated with adverse effects can be balanced with at least one marker for efficacy of thiazolidinedione therapy. Markers for HbA1c, a measure of efficacy of thiazolidinedione therapy, were also deduced using the 384 SNP array.

Figure 2:
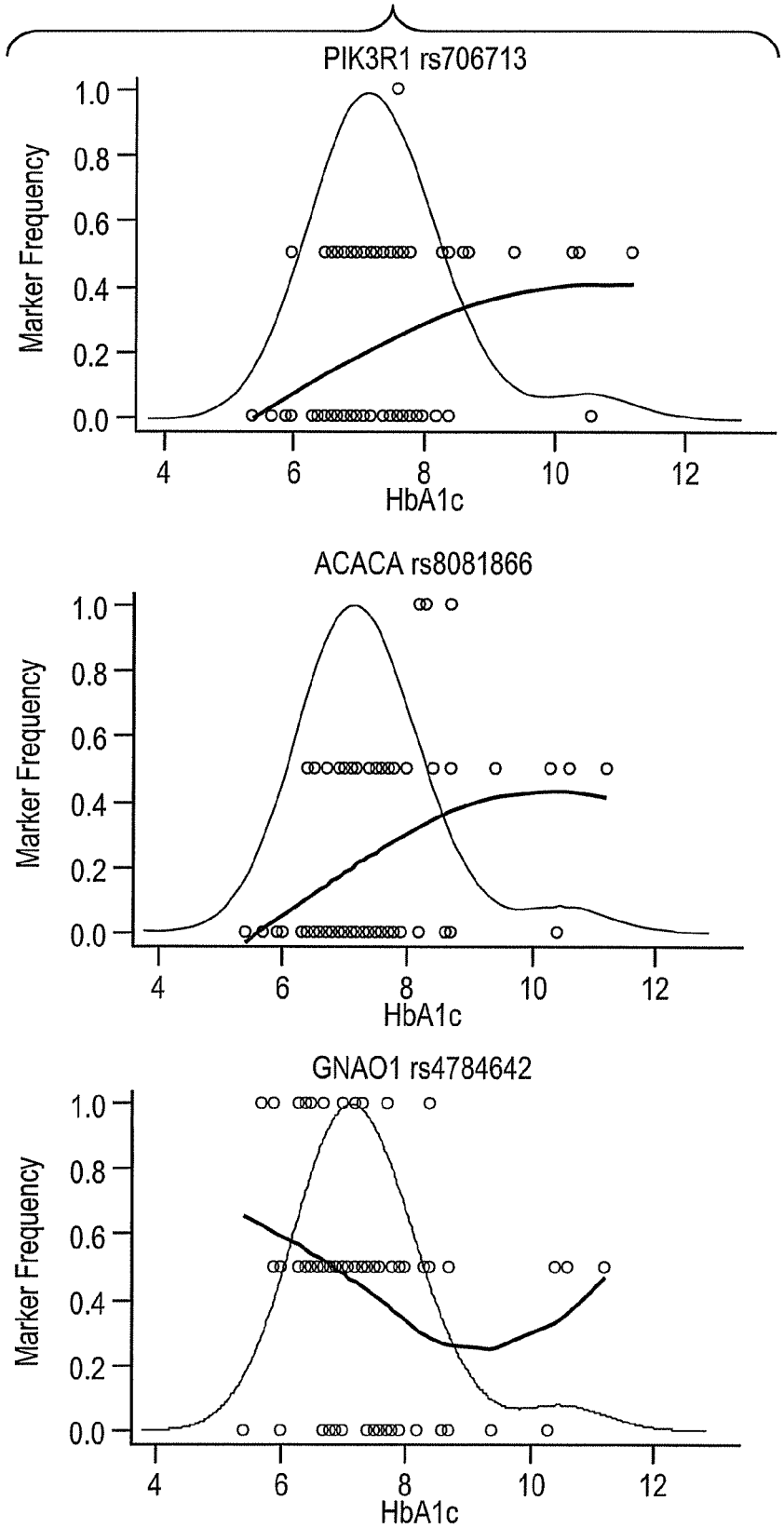
FIG. 2 shows individual genotypes (circles) of each SNP overlaid on the response distribution (thin line) for HbA1c.

In one embodiment, the physiogenomics plot, see e.g., FIGS. 2, 3, has a positive coefficient, that is, the slope increases with the increased frequency of the minor allele. In another embodiment, the physiogenomics plot has a negative coefficient, that is, the slope decreases with the increased frequency of the minor allele. In other embodiments, the marker is a neutral marker and the physiogenomics plot has a slope of about zero. When referring to a marker for risk of side effects, a marker with a positive coefficient is a risk marker and a marker with a negative coefficient is a protective marker. When referring to efficacy of therapy, a marker with a positive coefficient is associated with a lack of therapeutic effectiveness and a marker with a negative coefficient is associated with a positive therapeutic effect.

For the physiogenomic representation of the most significant genetic associations with BMI, each plot contains three components: the distribution of the phenotype (thin line), the genotype of each individual patient (circles) and the LOESS fit of the allele frequency as a function of phenotype (thick line). In each of three graphs, the abscissa represents each patient's weight (kg), which is the phenotype. The ordinate indicates the allele frequency for the LOESS curve. For clarity's sake, axis labels for the genotypes and the distribution curve are not shown. The genotypes are drawn on three levels: non-carriers of the minor allele at the bottom, single-carriers in the middle and double-carriers at the top. The scale for the distribution curve is arbitrary.

For the physiogenomic representation of marker frequency for edema, each plot contains the three most significant SNP associations. Patient counts (ordinate) are shown as a function of edema (abscissa) in individual plots for the nine genes. Allele counts of the most associated SNP for each gene are given numerically as minor allele/total alleles in the population (two for each patient). Allele frequencies are shown graphically with 95% confidence intervals based on the binomial distribution. The patient numbers differ slightly from panel to panel because of occasional missing genotype data.

In one embodiment, disclosed herein are markers and methods suitable for determining an individual at risk for, or protected from, BMI increase when undergoing thiazolidinedione therapy. For BMI, the 10 strongest associations were found with SNPs in genes involved in energy homeostasis, adiposity, glucose metabolism, lipid metabolism, and neurotransmission. Specifically, there is an association of BMI during thiazolidinedione therapy with polymorphisms in genes affecting adenosine, an adiponectin receptor, pyruvate kinase (muscle), and uncoupling protein 2.

In one embodiment, the marker for BMI increase is risk marker, including, for example, an SNP in the ADORA1 gene, the PKM2 gene, the ADIPOR2 gene, the UCP2 gene, the APOH gene, the IRS1 gene, or any combination thereof. In one embodiment, the marker for BMI increase is protective marker, including, for example, an SNP in the LIPA gene, the RARB gene, the CHRM3 gene, the APOA4 gene, or any combination thereof.

The strongest risk marker association for BMI is rs903361, a SNP found in intron 2 in the ADORA1 gene. Intronic polymorphisms may correlate with expression variation. In rodents, signaling from this receptor inhibits lipolysis in white and brown fat, induces insulin resistance in skeletal muscle, and increases insulin sensitivity in adipose tissue. Human studies have also implied the receptor in obesity. The next strongest risk marker association is to the muscle pyruvate kinase gene (PKM2). A glycolytic enzyme, pyruvate kinase M2, is involved in intracellular glucose regulation. Another gene associated with risk of BMI increase is the adiponectin receptor 2 gene. Adiponectin receptors 1 and 2 serve as receptors for globular and full-length adiponectin and mediate increased AMPK and PPAR-alpha (PPARA) ligand activities, as well as fatty acid oxidation and glucose uptake. A variant in the adiponectin receptor type 2 (ADIPOR2) gene, expressed in skeletal muscle and liver, is associated with type II diabetes. ADIPOR2 is associated with peroxisome proliferator activated receptors (PPAR), the gamma version of which is the target for thiazolidinedione therapy.

Other risk marker associations with unadjusted significance levels near $p=0.01$ were found including UCP2, APOH, IRS1, and LIPA. For some of these genes, metabolic roles relevant to adiposity are well established. UCP2 encodes for uncoupling protein 2, a mitochondrial protein involved in the control of the metabolism of fatty acids. UCP2 is associated predominantly with BMI, a finding consistent with its known, central role in energy balance, body weight, obesity, and thermoregulation. UCP2 variants may predispose to obesity. APOH is implicated in lipoprotein metabolism, coagulation, and the production of antiphospholipid autoantibodies. An APOH polymorphism is associated with variations in total and LDL cholesterol levels. The IRS1 gene encodes for insulin receptor substrate-1. A common functional mutation of IRS1 is G972R, which impairs the ability of insulin to stimulate glucose transport, glucose transporter translocation, and glycogen synthesis by affecting the PI3 kinase/AKT/GSK3 signaling pathway.

Protective marker associations include SNPs in the LIPA, RARB, CHRM3 and APOA4 genes. LIPA encodes for lysosomal acid lipase which connects extracellular with intracellular lipid metabolism and is the only hydrolase for cleavage of cholesteryl esters delivered to the lysosomes. Thus all of these genes are closely involved in metabolism. CHRM3 is the muscarinic acetylcholine receptor subtype M3 (CHRM3) gene which is expressed in islet β-cells and has a role in stimulating insulin secretion. APOAIV (APOA4) participates in the regulation of energy storage. For example hypothalamic APOA4 is regulated by leptin. With regard to RAR-Beta, retinoic acid receptors are members of the large family of nuclear receptors or transcription factors. The expression of RARB in the liver and colon responds to the feeding of specific nutrients. Gene expression changes of the RAR family have been noted with seasonal changes in body weight.

Specific risk markers related to BMI increase include markers closely linked to rs903361 (ADORA1), rs2856929 (PKM2), rs7975375 (ADIPOR2), rs660339 (UCP2), rs8178847 (APOH), rs4675096 (IRS1), and combinations comprising one or more of the foregoing markers. Specific protective markers related to BMI increase include markers closely linked to rs6586179 (LIPA), rs322695 (RARB), rs7520974 (CHRM3), rs675 (APOA4), and combinations comprising one or more of the foregoing markers.

In one embodiment, specific risk markers related to BMI increase include rs903361 (ADORAL; SEQ ID NO: 1), rs2856929 (PKM2), rs7975375 (ADIPOR2), rs660339 (UCP2), rs8178847 (APOH), rs4675096 (IRS1), and combinations comprising one or more of the foregoing markers. Specific protective markers related to BMI increase include rs6586179 (LIPA; SEQ ID NO: 7), rs322695 (RARB), rs7520974 (CHRM3), rs675 (APOA4), and combinations comprising one or more of the foregoing markers. The minor allele at position 22 of SEQ ID NO: 1 is G and the minor allele at position 22 of SEQ ID NO: 7 is A.

In one embodiment, the markers for determining an individual at risk for BMI increase when undergoing thiazolidinedione therapy include one or more risk markers and one or more protective markers. In one embodiment, risk markers are selected from a maker closely linked to rs903361 (ADORA1), rs2856929 (PKM2), rs7975375 (ADIPOR2), rs660339 (UCP2), rs8178847 (APOH), rs4675096 (IRS1), and combinations comprising one or more of the foregoing markers. In another embodiment, protective markers are selected from rs6586179 (LIPA), rs322695 (RARB), rs7520974 (CHRM3), rs675 (APOA4), and combinations comprising one or more of the foregoing markers. In one embodiment, risk markers are selected from rs903361 (ADORA1), rs2856929 (PKM2), rs7975375 (ADIPOR2), rs660339 (UCP2), rs8178847 (APOH), rs4675096 (IRS1), and combinations comprising one or more of the foregoing markers. In another embodiment, protective markers are selected from rs6586179 (LIPA), rs322695 (RARB), rs7520974 (CHRM3), rs675 (APOA4), and combinations comprising one or more of the foregoing markers.

In one embodiment, the risk marker related to BMI increase is a marker in the ADORA1 gene, such as a marker closely linked to rs903361, and the protective marker is a marker in the CHRM3 gene, such as a marker closely linked to rs7520974.

Exemplary markers closely linked to, that is, in the same haplotype as rs903361 (ADORA1) are rs6427990, rs6701725, rs12135643, rs3898276, rs12143879, and rs4570461. Exemplary markers closely linked to, that is, in the same haplotype as rs7520974 (CHRM3) are rs10926012, rs6669810, rs12078376, rs17658129, and rs12036109.

In one embodiment, disclosed herein are markers and methods suitable for determining an individual at risk for, or protected from, developing edema when undergoing thiazolidinedione therapy. The 10 SNPs associated with edema were found among genes involved in neurotransmission, vascular inflammation or regulation, lipid metabolism, glucose metabolism, and metabolism.

In one embodiment, the risk marker for edema is an SNP in the NPY gene, the GSY1 gene, the OLR1 gene, the ADRB gene, the SCARB2 gene, the HRH3 gene, the ACE gene, or a combination thereof. In another embodiment, the protective marker for edema is an SNP in the CCL2 gene, the GHRH gene), the ACACB gene, or a combination thereof.

The most significant association for edema is through neuropeptide Y (NPY). Though NPY is a long-lasting constrictor agent, it also enhances endothelial permeability with roles in neurogenic pulmonary edema, edema of the larynx, and together with dipeptidyl-peptidase IV (DPP4, CD26) is involved in inflammatory paw edema in rats. Other genes with SNP associations close to p<0.01 include CCL2 (MCP-1), GYS1, and OLR1. Chemokine (C-C motif) ligand 2 (CCL2) increases the permeability of the blood-brain barrier and participates in vasogenic brain edema. ORL1 expresses the oxidized low density lipoprotein receptor 1 in vascular endothelial cells where it participates in capillary formation.

In contrast, edema induced by thiazolidinedione therapy is associated with polymorphisms in genes controlling vascular permeability.

Specific markers related to edema are selected from markers closely linked to rs1468271 (NPY), rs2287754 (GYS1), rs2742115 (OLR1), rs2429511 (ADRB1), rs894251 (SCARB2), rs1614845 (HRH3), rs4333 (ACE), rs3760396 (CCL2), rs6032470 (GHRH), rs34274 (ACACB), and combinations comprising one or more of the foregoing markers. In one embodiment, markers related to edema are selected from rs1468271 (NPY), rs2287754 (GYS1), rs2742115 (OLR1), rs2429511 (ADRB1), rs894251 (SCARB2), rs1614845 (HRH3), rs4333 (ACE), rs3760396 (CCL2), rs6032470 (GHRH), rs34274 (ACACB), and combinations comprising one or more of the foregoing markers.

In one embodiment, the markers for determining an individual at risk for edema when undergoing thiazolidinedione therapy include one or more risk markers and one or more protective markers. In one embodiment, risk markers are selected from markers closely linked to rs1468271 (NPY), rs2287754 (GYS1), rs2742115 (OLR1), rs2429511 (ADRB1), rs894251 (SCARB2), rs1614845 (HRH3), rs4333 (ACE), and combinations comprising one or more of the foregoing markers. In another embodiment, protective markers are selected from markers closely linked to rs3760396 (CCL2), rs6032470 (GHRH), rs34274 (ACACB), and combinations comprising one or more of the foregoing markers.

In one embodiment, risk markers related to edema are selected from rs1468271 (NPY), rs2287754 (GYS1), rs2742115 (OLR1), rs2429511 (ADRB1), rs894251 (SCARB2), rs1614845 (HRH3), rs4333 (ACE), and combinations comprising one or more of the foregoing markers. In another embodiment, protective markers are selected from rs3760396 (CCL2), rs6032470 (GHRH), rs34274 (ACACB), and combinations comprising one or more of the foregoing markers.

In one embodiment, the risk marker related to edema is a marker in the NPY gene, such as a marker closely linked to rs1468271, and the protective marker is a marker in the CCL2 gene, such as a marker closely linked to rs3760396.

Exemplary markers closely linked to, that is, in the same haplotype as rs1468271 (NPY) are rs7800861, rs10256432, rs3857723, rs16479, rs13223753, rs3025121, rs3025124, rs16141, rs5576, rs16135, rs4719762, rs10241609, rs16148, and rs16475. Exemplary markers closely linked to, that is, in the same haplotype as rs3760396 (CCL2) are rs991804, rs3091318, rs4795893, rs17652343, rs2857653, rs2857655, rs8079244, rs2190970, rs3760399, rs2530797, and rs3917878.

As a marker for the efficacy of thiazolidinedione therapy, glycosylated or glycated hemoglobin (HbA1c) has been selected. HbA1c is a form of hemoglobin used primarily to identify the plasma glucose concentration over prolonged periods of time. Glycation of hemoglobin has been implicated in nephropathy and retinopathy in diabetes mellitus. HbA1c is frequently monitored in diabetic patients as a measure of the efficacy of treatment.

In one embodiment, the marker for HbA1C is an SNP in the PIK3R1 gene, the ACACA gene, the GNAO1 gene, the EDN1 gene, the INSR gene, the LIPC gene, the GAD1 gene, the HIF1A gene, the BDNF gene, the ACAT1 gene, the UCP2 gene, or a combination thereof.

The top hit for HbA1c is rs706713, a synonymous SNP in phosphoinositide-3-kinase, regulatory subunit 1 (PIK3R1). PIK3R1 is the p85 regulatory subunit of the Class 1A PI 3-kinase, which plays a pivotal role in the insulin signaling pathway. Another hit is rs8081866, in acetyl-Coenzyme A carboxylase alpha (ACACA). ACACA has an important role in fatty acid metabolism and regulation. Involved in signal transmission, GNAO1 is a G-protein not previously linked with obesity, diabetes, or insulin signaling.

Specific markers related to HbA1C level are selected from markers closely linked to rs706713 (PIK3R1), rs8081866 (ACACA), rs4784642 (GNAO1), rs5369 (EDN1), rs4804103 (INSR), rs6083 (LIPC), rs3791850 (GAD1), rs2049045 (BDNF), rs6265 (BDNF), rs11212515 (ACAT1), rs10890819 (ACAT1), rs891087 (INSR), rs2301108 (HIF1A), rs1128503 (ABCB1), rs660339 (UCP2), rs1801701 (APOB), and combinations comprising one or more of the foregoing markers.

In one embodiment, markers related to HbA1C level are selected from rs706713 (PIK3R1), rs8081866 (ACACA), rs4784642 (GNAO1), rs5369 (EDN1), rs4804103 (INSR), rs6083 (LIPC), rs3791850 (GAD1), rs2049045 (BDNF), rs6265 (BDNF), rs11212515 (ACAT1), rs10890819 (ACAT1), rs891087 (INSR), rs2301108 (HIF1A), rs1128503 (ABCB1), rs660339 (UCP2), rs1801701 (APOB) and combinations comprising one or more of the foregoing markers.

In one embodiment, the markers for determining the effectiveness of thiazolidinedione therapy include one or more risk markers and one or more protective markers. In one embodiment, risk markers are selected from markers closely linked to rs10515070 (PIK3R1), rs4804103 (INSR), rs706713 (PIK3R1), rs8081866 (ACACA), rs6083 (LIPC), rs3791850 (GAD1), rs891087 (INSR), rs2301108 (HIF1A), or rs1801701 (APOB), and combinations comprising one or more of the foregoing markers. In another embodiment, protective markers are selected from markers closely linked to rs4784642 (GNAO1), rs5369 (EDN1), rs3791850 (GAD1), rs1128503 (ABCB1), or rs660339 (UCP2), and combinations comprising one or more of the foregoing markers.

In one embodiment, risk markers are selected from rs10515070 (PIK3R1), rs4804103 (INSR), rs706713 (PIK3R1), rs8081866 (ACACA), rs6083 (LIPC), rs3791850 (GAD1), rs891087 (INSR), rs2301108 (HIF1A), or rs1801701 (APOB), and combinations comprising one or more of the foregoing markers. In another embodiment, protective markers are selected from rs4784642 (GNAO1), rs5369 (EDN1), rs3791850 (GAD1), rs1128503 (ABCB1), or rs660339 (UCP2), and combinations comprising one or more of the foregoing markers.

In one embodiment, the risk marker is a marker closely linked to rs10515070 (PIK3R1), rs4804103 (INSR), rs706713(PIK3R1), rs8081866 (ACACA), rs6083 (LIPC), rs3791850 (GAD1), rs891087 (INSR), rs2301108 (HIF1A), or rs1801701 (APOB); and the protective marker is a marker closely linked to rs4784642 (GNAO1), rs5369 (EDN1), rs3791850 (GAD1), rs1128503 (ABCB1), or rs660339 (UCP2), and combinations comprising one or more of the foregoing markers.

In one embodiment, the risk marker for the efficacy of thiazolidinedione therapy is a marker in the PIK3R1 gene, such as a marker closely linked to rs706713, and the protective marker is a marker in the GNAO1 gene, such as a marker closely linked to rs4784642. Exemplary markers closely linked to, that is, in the same haplotype as rs706713 (PIK3R1) are rs40419, rs10940157, rs6449959, rs7713645, rs16897471, rs11749932, rs4639168, and rs16897511.

Exemplary markers closely linked to, that is, in the same haplotype as rs4784642 (GNAO1) are rs1209158, rs1210083, rs2060680, rs8063585, rs2895070, rs16956168, rs12920563, rs929872, rs1190761, rs12924617, rs6499829, rs16956111, rs7205824, rs11641551, and rs11649418.

A table containing all of the SNPs associated with thiazolidinedione therapy is given below:

TABLE 1

List of markers

| SEQ ID NO: | SNP | Gene | Sequence |
|---|---|---|---|
| 1 | rs903361 | ADORA1 | agtggtcagg cttcacccag trctacagag cagatctggg ac |
| 2 | rs2856929 | PKM2 | caggctcagg gtctaaattc crtatcctttt cttccatacc ct |
| 3 | rs7975375 | ADIPOR2 | cttttcacag gaaaatttct trggagtcta ttgtcactgt ct |
| 4 | rs660339 | UCP2 | acaccgcggt actgggcgct grctgtagcg cgcactggcc cc |
| 5 | rs8178847 | APOH | tacctacgtt tgcaacactt crtgtttata agccatcagc tg |
| 6 | rs4675096 | IRS1 | agtgttttcc aaggtgtgat traaaatgga gatttcttac ct |
| 7 | rs6586179 | LIPA | accctgcatt ctgaggggtc trgagggaaa ctgacagctg tg |
| 8 | rs322695 | RARB | cctgtaggat tgtgttcctc traaactgtc ccctaaatta tg |
| 9 | rs7520974 | CHRM3 | cagctgaaag aaagacaaat artagatacc cactgcatgg ct |
| 10 | rs675 | APOA4 | gagaaagaga gccaggacaa gwctctctcc ctccctgagc tg |
| 11 | rs1468271 | NPY | gaccctgtaa ttttcagaaa crcacatagg agtgggtgtc tg |
| 12 | rs2287754 | GYS1 | cgggaagctt gcaagacgct crgcttccta ttgcaagacc gc |
| 13 | rs2742115 | OLR1 | acatgtgtac acgtggtgta trttaaaaac ttcaggctct ct |
| 14 | rs2429511 | ADRB1 | tcctggcttc cttctggacc crcaaggggc agtctcaaaa ta |
| 15 | rs894251 | SCARB2 | ctcaggaggc cttactgtgc crtggttctt gcccttttgat tt |
| 16 | rs1614845 | HRH3 | aagctgctgt aaatggaggc trcctagaga ggagagggcc tg |
| 17 | rs4333 | ACE | ctgaccccaa gagcgagggg arcccaactc tgtgctctca cc |
| 18 | rs3760396 | CCL2 | gacagagaga ggacccaagc asgcaactag ttgaggact tg |
| 19 | rs6032470 | GHRH | agccccagtc cttaccggaa crgtagaggc ttaacaaaca tt |
| 20 | rs34274 | ACACB | ctctatgatt tcacagtgat grgctcaagt atgtgtctgc tt |
| 21 | rs706713 | PIK3R1 | tttccttcca atatattcta crtaagttcc cggaaagtcc cc |
| 22 | rs10515070 | PIK3R1 | agattcctcc ctgtacgata gwgtcttact tttccactt gc |
| 23 | rs8081866 | ACACA | gagaagctcc catctagctg trtatgatag ggggtttatc tg |
| 24 | rs4784642 | GNAO1 | attttcttct gggtggccct aractgcttt cttttttcccc at |
| 25 | rs5369 | EDN1 | cacaaaggca acagaccgtg araatagatg ccaatgtgct ag |
| 26 | rs4804103 | INSR | tcctgtgaga gagttgagag crataatttt agggtggtta tt |
| 27 | rs6083 | LIPC | gtctttctcc agatgatgcc artttttgtgg atgccattca ta |
| 28 | rs3791850 | GAD1 | cacaacaagg gtttagctct argggagagca gaggcaggat ga |
| 29 | rs2049045 | BDNF | aaatctctct tcttcgataa asttcccagg aggtaaccca at |
| 30 | rs6265 | BDNF | ttggctgaca ctttcgaaca crtgatagaa gagctgttgg at |
| 31 | rs11212515 | ACAT1 | ggattgcaat aaagggaagg awgaaggatg attttggctt ga |
| 32 | rs10890819 | ACAT1 | accagaagct agcataatgg artatcgccc ctcactttgt tc |

TABLE 1-continued

List of markers

| SEQ ID NO: | SNP | Gene | Sequence |
|---|---|---|---|
| 33 | rs891087 | INSR | gcaggtctcc acacacctgc crtccaggta gaagttgcgg ca |
| 34 | rs2301108 | HIF1A | ctactggaag attagccacg trttgagttt tgtcttttgca tt |
| 35 | rs1128503 | ABCB1 | actctgcacc ttcaggttca grcccttcaa gatctancag ga |
| 36 | rs660339 | UCP2 | acaccgcggt actgggcgct grctgtagcg cgcactggcc cc |
| 37 | rs1801701 | APOB | tcagatggaa aaatgaagtc crgattcatt ctgggtcttt cc |

In one embodiment, the identified novel genotypes can further be developed into "physiotypes" from combinations of contributory gene polymorphisms and baseline physiological characteristics. Physiotypes are predictive models incorporating genotypes from various genes and covariates (e.g., baseline serum levels and clinical examination) and integrate the combined information of genotype and phenotype. Physiotypes are derived from different genes in interacting pathways, which allow sampling of the genetic variability in entire physiological networks. Although an individual's genotype does not change, other physiological characteristics may influence the individual's phenotype and may alter the physical response to thiazolidinedione therapy based on interacting physiological pathways. Physiotypes have utility in personalized medical treatment and facilitate the assessment of accurate risk-benefit-ratios for medical management of type 2 diabetes.

The disclosed methods include assessing an individual for the presence or absence of risk and/or protective markers, that is, genotyping the individual for protective and/or risk markers. Assessing the individual includes, for example, assaying genetic material from the individual. In one embodiment, genetic material includes nucleic acid, e.g., DNA from a blood sample of a subject, and assaying includes assaying the nucleic acid to determine the individual's genotype of one or a combination of the marker genes associated with efficacy and/or safety of thiazolidinedione therapy. Other sampling procedures include but are not limited to buccal swabs, saliva, or hair root. In a specific embodiment, genotyping is performed using a gene array methodology, which can be readily and reliably employed in screening and evaluation methods. A number of gene arrays are commercially available for use by the practitioner, for example, but not limited to, static (e.g., photolithographically set), suspended (e.g., soluble arrays), and self assembling (e.g., matrix ordered and deconvoluted). More specifically, the nucleic acid array analysis allows the establishment of a pattern of gene expression variability from multiple genes and facilitates an understanding of the complex interactions that are elicited in an individual in response to a drug or treatment, such as thiazolidinedione therapy.

In a specific embodiment, an array comprises several hundred genes and is capable of genotyping hundreds of DNA polymorphisms simultaneously. Candidate genes for use in the arrays are identified by various means including, but not limited to, pre-existing clinical databases and DNA repositories, review of the literature, and consultation with clinicians, differential gene expression models of weight increase and edema, physiological pathways in thiazolidinedione metabolism, pathways affecting adenosine, an adiponectin receptor, pyruvate kinase (muscle), uncoupling protein 2, and pathways controlling vascular permeability. In one embodiment, the candidate genes are selected from those shown in Tables 4-7. The gene array includes all of the novel marker genes, or a subset of the genes, or unique nucleic acid portions of these genes. The gene array is useful in discovering new genetic markers of susceptibility to efficacy of thiazolidinedione drugs and/or side effects including BMI increase and edema.

In another embodiment, provided herein is a screening method to allow the identification of subsets of individuals who have specific genotypes and physiological characteristics and are susceptible to the efficacy and/or safety of thiazolidinedione therapy. For example, a screening method of this embodiment involves assessing an individual by employing an assay method, e.g., an array system and newly-identified marker genes and gene variants as described herein, to evaluate whether the individual has a genotype associated with efficacy and/or safety of thiazolidinedione therapy. In a specific embodiment, more than one SNP is used to determine if a patient is susceptible to the efficacy and/or safety of thiazolidinedione therapy. In a more specific embodiment, the more than one SNP comprises at least one SNP with a positive coefficient (e.g., risk marker) and at least one SNP with a negative coefficient (e.g., protective marker). The physiogenomics method mathematically assigns to each SNP a coefficient according to pre-established rules and covariates. The generation of the coefficients is discussed in detail in the examples and in U.S. patent application Ser. No. 11/371, 511 and U.S. patent application Ser. No. 11/010,716, both of which are incorporated by reference herein. The coefficient for each SNP is either positive, indicating that the presence of that marker contributes to physiological response or negative (i.e., protective marker). The most powerful predictions are achieved for a particular physiological endpoint by using SNPs having positive coefficients and SNPS having negative coefficients.

Individuals identified through screening using the methods disclosed herein would be especially amenable to specific treatments, therapies, or further study to improve efficacy or reduce side effects of thiazolidinedione therapy. Depending on the combinatorial genotype of the individual, the dose of thiazolidinedione may be lowered, the individual may be switched to a different class of drugs. Also, the side effects may be monitored and followed-up with prophylactic treatment. For example, if the individual is at risk of BMI increase, a strict diet may be indicated.

Yet another embodiment is to identify a population of patients at risk for BMI increase or edema caused by thiazolidinedione treatment to be used as a population to test and evaluate substances, e.g., compounds or drugs, to identify those substances that prevent or reduce BMI increase or edema caused by thiazolidinedione therapy. Substances that prevent BMI increase or edema caused by thiazolidinedione treatment are suitable for use in BMI increase or edema prophylaxis. The evaluation method employs one or more of the newly identified gene variants that have been discovered to be associated with BMI increase or edema effects during thiazolidinedione treatment as described herein. Thus, provided herein is a method for screening for a desired prophylactic or therapeutic compound by determining if the compound prevents or reduces BMI increase or edema caused by thiazolidinedione treatments in one or more individuals identified to be at risk for such side effects.

In one embodiment, correlating the physiotype is performed by referencing a table, algorithm, nomogram, a web-based portal, or a downloadable guidance that includes correlations between alleles of the markers and a phenotype of interest. Suitable tables include a paper or electronic database comprising relevant correlation information. In one aspect, a database is a multidimensional database comprising multiple correlations and taking multiple correlation relationships into account, simultaneously. Accessing the table includes, for example, extracting correlation information or more complex statistical analysis, such as principle component analysis (PCA). In one embodiment, the physiotypes are used to form objective rules in a rules-based medicine analysis.

In another embodiment, a diagnostic kit containing a support or support material, such as, without limitation, a nylon or nitrocellulose membrane, bead, or plastic film, or glass, or micro-or nano-array, comprising the novel set of genes as described herein, in a form suitable for the practitioner to employ in screening individuals. The kit can contain the novel gene marker set associated with an increased risk for thiazolidinedione-induced BMI increase or edema, or a subset of these genes, on a suitable substrate or micro-or nano-array. In addition, the kit can optionally contain other materials necessary for carrying out the assay method, including, but not limited to, labeled or unlabeled nucleic acid probes, detection label, buffers, controls, and instructions for use.

The following examples further illustrate the invention but, of course, should not be construed as in any way limiting its scope. In particular, the processing conditions are merely exemplary and can be readily varied by one of ordinary skill in the art.

EXAMPLES

Experimental Protocols:
Study Sample

Outpatients with type 2 diabetes treated between February and June 2007 with rosiglitazone (n=54) or pioglitazone (n=33) for ≧4 months at the Joslin Diabetes Center affiliate of The Hospital of Central Connecticut (THOCC) in New Britain, Conn. were recruited as volunteer subjects. There were no exclusionary criteria. Each subject provided informed written consent as approved by the THOCC Institutional Review Board.

Data Collection

Clinical Assessment. Patient characteristics included age, height, weight, body mass index, and the presence/absence of edema as recorded by a physician.

Blood Collection. Blood for DNA extraction was either prospectively collected or retrieved from routine clinical analysis. Samples were collected into tubes containing either EDTA or citrate buffer. The DNA was extracted from leulocytes in 1 ml of whole blood using the Gentra Puregene® DNA isolation kit.

Laboratory Analyses

Genotyping Technology and Assay. Genotyping was performed using the Illumina BeadArray™ platform and the GoldenGate™ assay.

Hemoglobin $A_{1c}$: HbA1c levels were measured via ion exchange using the HPLC Variant II (BioRad Laboratories, Hercules Calif.).

Physiogenomics (PG) Array. A Physigenomic Array including 384 SNPs from 222 genes has been designed and tested. The PG Array has been applied to about 4,000 patients in various clinical studies. Representative genes included in the PG Array are shown in Table 2. The following pathways are represented: insulin resistance, glucose metabolism, energy homeostasis, adiposity, apolipoproteins and receptors, fatty acid and cholesterol metabolism, lipases, receptors, cell signaling and transcriptional regulation, growth factors, drug metabolism, blood pressure, vascular signaling, endothelial dysfunction, coagulation and fibrinolysis, vascular inflammation, cytokines, neurotransmitter axes (serotonin, dopamine: cholinergic, histamine, glutamate) and behavior (satiety). Public databases (dbSNP, ensemb1) were searched for validated SNPs with known allele frequencies for mixed or Caucasian populations. SNPs were selected with minor allele frequency between 10% and 30%, avoiding higher allele frequencies because such SNPs are more likely to be phenotypically neutral. The full listing of genes and SNPs in the PG AlTay has been published as part of U.S. patent publication no. 2006/0278241.

TABLE 2

Selected representative genes and pathways relevant to thiazolidinedione response from the Physiogenomic (PG) Array. The PG Array consists of 222 genes and 384 SNPs. The PG Array is proprietary to Genomas.

| | |
|---|---|
| Insulin Resistance: insulin, insulin receptor, insulin receptor substrate 1, Akt1, Akt2, cholecystokinin and cholecystokinin receptor A and B, resistin, regulatory subunit of PI3-kinase (polypeptide 1, p85α), ATP-binding cassette B1, C8, and G5 | Growth factors: insulin-like growth factor 1, growth hormone 1, growth hormone releasing hormone, transforming growth factor |
| | Cell signaling: catalytic PI3K α, β, γ, δ polypep, class 2 PI3K β, γ polypep, class 3 PI3K, catalytic PI3K, α polypep |
| Glucose Metabolism: glucagon, glycogen synthase 1, 2, 3β, phosphofructokinase (liver, muscle, platelet), pyruvate kinase (liver, RBC, muscle), phosphoenolpyruvate carboxykinase 1 | Vascular signaling: vascular endothelial growth factor A, VEGF receptor (KDR), angiopoietin 1, 2, TEK tyrosine kinase, adenosine receptors A1, A2a, A2b, A3 |
| Energy Homeostasis: uncoupling protein 2 and 3, adrenergic receptor α1A, α2A, α2B, β1, β2, β3, carnitine palmitoyltransferase 1A, 1B, 2, melanocortin receptor 3 and 4, pro-opiomelanocortin, malate dehydrogenase, AMP kinase, subunit α1, catalytic AMP-activated protein kinase α-2, non-catalytic AMP-activated protein kinase β1, β2, γ1, 2, 3, thioredoxin reductase 2 | Transcriptional regulation: peroxisome proliferation-activated receptor α, γ, hypoxia-inducible factor 1A, sterol regulatory element binding transcription factor 1, retinoic receptor α, β, γ; α, β, γ, WBSCR14 |
| | Adrenal function: glucocorticoid receptor, corticotropin releasing hormone and receptor 1 and 2 |
| | Apoptosis: tumor necrosis factor (TNF), AVEN |
| Adiposity: leptin receptor, ghrelin precursor, adiponectin receptor 1 and 2, adipocyte | Cytochrome P450: 1A2, 2C19, 2D6, 2C9, 3A4, 3A5, 7 |
| | Fatty acid homeostasis: acetyl-CoA- |

TABLE 2-continued

Selected representative genes and pathways relevant to thiazolidinedione response from the Physiogenomic (PG) Array. The PG Array consists of 222 genes and 384 SNPs. The PG Array is proprietary to Genomas.

| | |
|---|---|
| Lipases: hepatic, lipoprotein, hormone-sensitive, lysosomal acid, endothelial, and gastric | acetyltransferase 1, 2, acetyl-CoA carboxylase α, β, CETP, LCAT, fatty acid synthase, fatty acid-binding protein 2, microsomal triglyceride transfer protein, paraoxonase 1, choline kinase beta, HMG-CoA reductase |

Statistical Analysis

Physiogenomic Analysis. Patients treated with rosiglitazone or pioglitazone were recruited from THOCC clinics and provided informed written consent as approved by the THOCC Institutional Review Board. For physiogenomic associations to HbA1c, body mass index and edema, genotype data were obtained on 88 patients, 55 on rosiglitazone and 33 on pioglitazone regimens. A standardized set of phenotypes were collected from the most recent medical records for each patient. Valid genotype data were obtained on the 88 patients. Extensive information on co-medications and disease history were also collected to control for environmental effects.

Figure 1:
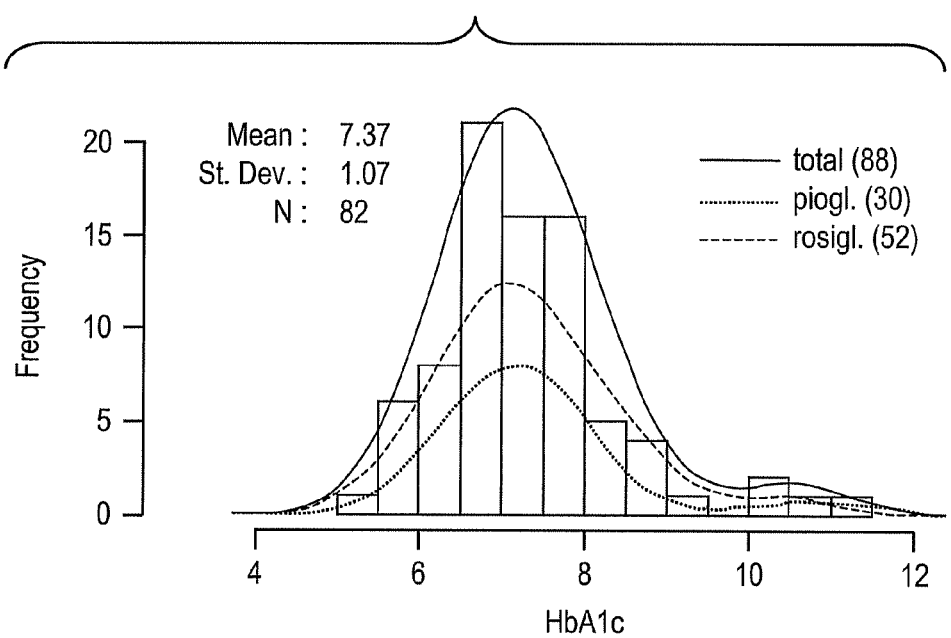
FIG. 1 shows the population distributions for glycosylated hemoglobin (HbA1c) and body mass index (BMI).
Figure 1:
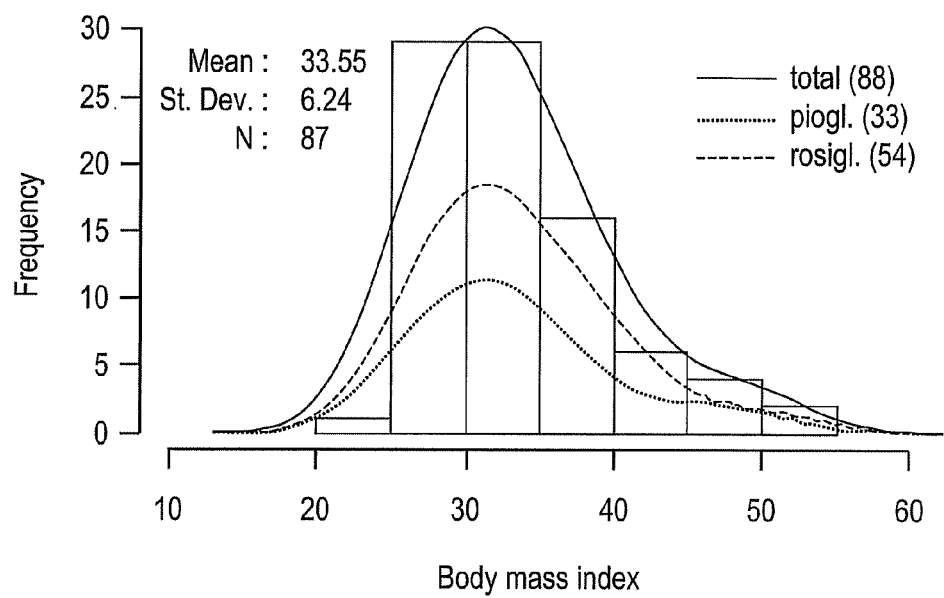

HbA1c was selected as an indicator for efficacy, and body mass index and edema as indicators of undesired side effect. Table 3 shows the averages of these phenotypes among different sections of the population. FIG. 1 shows the population distributions graphically for HbA1c and BMI. There was a 16% incidence of edema in this population. None of the responses were significantly different between the drug groups. The phenotypes were analyzed for covariate dependence on age, gender, ethnicity, and treatment. Using linear regression and ANOVA, it was found that none of these covariates had a significant effect on the phenotypes, except a marginally significant contribution of 5% to the BMI variation by age (p=0.035), with BMI decreasing by 0.15 points for each year of age.

TABLE 3

Phenotypes by covariates. Data for BMI and edema are means.

| Covariate | Value | N | HbA1c [%] | BMI |
|---|---|---|---|---|
| All | all | 88 | 7.4 | 33.6 |
| Gender | female | 30 | 7.3 | 36.1 |
| Gender | male | 58 | 7.4 | 32.3 |
| Age | 30-40 | 2 | 8.7 | 44.2 |
| Age | 40-50 | 12 | 7.8 | 32.6 |
| Age | 50-60 | 22 | 7.5 | 35.3 |
| Age | 60-70 | 33 | 7.3 | 33.0 |
| Age | 70-80 | 14 | 7.3 | 33.1 |
| Age | >80 | 5 | 6.6 | 29.1 |
| Ethnicity | African Amer. | 4 | 7.9 | 36.8 |
| Ethnicity | Caucasian | 83 | 7.3 | 33.5 |
| Ethnicity | Hispanic | 1 | 7.8 | 25.2 |
| Drug | pioglitazone | 33 | 7.4 | 33.4 |
| Drug | rosiglitazone | 55 | 7.4 | 33.7 |

Edema as a Phenotype. In contrast to BMI, which is a continuous scaled variable, the endpoint of edema has a discrete, non-normal distribution, so a linear regression test based on the F-distribution is not automatically valid. To establish validity, an independent calculation of the p-values was performed using permutation testing. Permutation testing requires extensive computation, but the resulting p-values are non-parametric, i.e., they are valid regardless of the endpoint distribution. The agreement between permutation p-values and those from the F-distribution was very good ($R^2$=98%, RMSD=0.055).

Physiogenomic PG Plot. To demonstrate the association of an SNP marker with any given quantitative phenotype, the allele frequency was plotted as a function of phenotype using the LOESS fit. LOESS (LOcally wEighted Scatter plot Smooth) is a method to smooth data using a locally weighted linear regression. At each point in the plot, a quadratic polynomial is fitted to the data in the vicinity of that point. The data are weighted such that they contribute less if they are further away, according to the tricubic function (Box), where x is the abscissa of the point to be estimated, $x_i$ are the data points in the vicinity, and d(x) is the maximum distance of x to $x_i$.

$$w_i = \left(1 - \left|\frac{x - x_i}{d(x)}\right|^3\right)^3$$

Example 1

Physigenomics Analysis

A total of 346 SNPs were tested for association of minor allele copy number (0, 1, or 2) with the covariate adjusted endpoints using linear regression. The SNPs were ranked by the F-statistic p-value of the genotype coefficient, and false discovery rates (FDR) were calculated. Tables 4-6 show the 5 most significant associations for the 3 phenotypes.

TABLE 4

Top 5 SNP associations to HbA1c.

| SNP | Gene | p-value | FDR | SNP type | Gene Name |
|---|---|---|---|---|---|
| rs706713 | PIK3R1 | 0.001 | 0.35 | exon 1, Y73Y | phosphoinositide-3-kinase, regulatory subunit 1 |
| rs8081866 | ACACA | 0.012 | 0.99 | intron 28 | acetyl-Coenzyme A carboxylase alpha |
| rs4784642 | GNAO1 | 0.013 | 0.99 | 2 kb upstream | G protein, alpha activating activity polypeptide O |
| rs5369 | EDN1 | 0.014 | 0.99 | exon 3, E106E | endothelin 1 |
| rs4804103 | INSR | 0.016 | 1.00 | intron 2 | insulin receptor |

TABLE 5

Top 5 SNP associations to BMI.

| SNP | Gene | p-value | FDR | SNP type | Gene Name |
|---|---|---|---|---|---|
| rs903361 | ADORA1 | 3E−04 | 0.10 | intron 2 | adenosine A1 receptor |
| rs2856929 | PKM2 | 0.002 | 0.55 | intron 7 | pyruvate kinase, muscle |
| rs7975375 | ADIPOR2 | 0.007 | 0.92 | intron 1 | adiponectin receptor 2 |
| rs660339 | UCP2 | 0.008 | 0.94 | exon 2, V55A | uncoupling protein 2, mitochondrial proton carrier |

TABLE 6

Top 5 SNP associations to edema.

| SNP | Gene | p-value | FDR | SNP type | Gene Name |
|---|---|---|---|---|---|
| rs1468271 | NPY | 0.006 | 0.88 | intron 1 | neuropeptide Y |
| rs2287754 | GYS1 | 0.013 | 0.99 | 5' UTR | glycogen synthase 1 (muscle) |
| rs3760396 | CCL2 | 0.015 | 0.99 | 500 bp upstream | chemokine (C-C motif) ligand 2 |
| rs2742115 | OLR1 | 0.015 | 1.00 | intron 1 | oxidized low density lipoprotein receptor 1 |
| rs6032470 | GHRH | 0.023 | 1.00 | 2 kb upstream | growth hormone releasing hormone |

The top hit for HbA1c is rs706713, a synonymous SNP in phosphoinositide-3-kinase, regulatory subunit 1 (PIK3R1) (FIG. 2). PIK3R1 is the p85 regulatory subunit of the Class 1A PI 3-kinase, which plays a pivotal role in the insulin signaling pathway. Another hit is rs8081866, in acetyl-Coenzyme A carboxylase alpha (ACACA). ACACA has an important role in fatty acid metabolism and regulation. A third hit, GNAO1, is a G-protein involved in signal transmission and was not previously linked with obesity, diabetes, or insulin signaling.

For BMI, associations were observed for SNPs located within or near the following genes and their pathways: three representing energy homeostasis, including ADORA1 (adenosine A1 receptor), UCP2 (uncoupling protein 2), and RARB (retinoic acid receptor, beta); one gene regulating adiposity, ADIPOR2 (adiponectin receptor 2); two genes that participate in glucose metabolism, including PKM2 (pyruvate kinase, muscle) and IRS1 (insulin receptor substrate-1); three genes regulating lipid metabolism, including APOH (aplipoprotein H), LIPA (lysosomal acid lipase A), and APOA4 (apolipoprotein A-IV), and a gene representing neurotransmission, CHRM3 (cholinergic receptor, muscarinic 3) (Table 7, top). The top hit for BMI, is rs903361, an intronic SNP in adenosine A1 receptor ADORAL (FIG. 3). In rodents, signaling from this receptor inhibits lipolysis in white and brown fat, induces insulin resistance in skeletal muscle, and increases insulin sensitivity in adipose tissue. Human studies have also implied the receptor in obesity. The next strongest hit is rs2856929, an intronic SNP in the muscle pyruvate kinase gene (PKM2). A glycolytic enzyme, pyruvate kinase M2 is involved in intracellular glucose regulation. Another marker associated with body mass index in our dataset is rs7975375, an intronic SNP in the adiponectin receptor 2 gene. Adiponectin receptors 1 and 2 serve as receptors for globular and full-length adiponectin and mediate increased AMPK and PPAR-alpha (PPARA) ligand activities, as well as fatty acid oxidation and glucose uptake.

For edema, associations were observed for SNPs in the following genes and pathways: two with roles in neurotransmission, including NPY (neuropeptide Y) and HRH3 (histamine receptor H3); three that participate in vascular inflammation or vascular regulation, including CCL2 (chemokine [C-C motif] ligand 2), OLR1 (oxidized LDL receptor 1), and ACE (angiotensin I converting enzyme 1); two that regulate lipid metabolism, including ACACB (acetyl-Coenzyme A carboxylase beta) and SCARB2 (scavenger receptor class B, member 2; a glucose metabolism gene SNP, GYS1 (glycogen synthase 1, [muscle]); a growth and metabolism gene, GHRH (growth hormone releasing hormone), and one with vascular and metabolic roles, ADRB1 (adrenergic, beta-1-, receptor) (Table 7, bottom). The top hit for edema is rs1468271, an intronic SNP in neuropeptide Y (NPY). NPY has been shown to enhance permeability across a rat aortic endothelial cell monolayer, and together with dipeptidyl-peptidase IV (DPP4, CD26) is known to be involved in inflammatory paw edema in rats. Chemokine (C-C motif) ligand 2 (CCL2, MCP-1) has been shown to increase the permeability of the blood-brain barrier and to be involved in vasogenic brain edema.

TABLE 7

Allele frequencies, p-values, coefficients and FDR p-values of the top 10 markers associated to BMI and edema. P-values less than 0.2 are shown in bold. Negative coefficients indicate protective marker status and positive, risk.

| Gene Name | Gene | SNP | MAF Study | MAF CEU | P-value BMI | P-value EDM | Coeff | FDR |
|---|---|---|---|---|---|---|---|---|
| BMI Markers | | | | | | | | |
| adenosine A1 receptor | ADORA1 | rs903361 | 33.0% | 32.0% | 0.0003 | 0.419 | 3.4 | 0.10 |
| pyruvate kinase, muscle | PKM2 | rs2856929 | 23.3% | 21.0% | 0.002 | 0.311 | 3.0 | 0.55 |
| adiponectin receptor 2 | ADIPOR2 | rs7975375 | 14.8% | 13.0% | 0.007 | 0.116 | 3.4 | 0.92 |
| uncoupling protein 2 | UCP2 | rs660339 | 36.4% | 38.0% | 0.008 | 0.068 | 2.4 | 0.94 |
| apolipoprotein H | APOH | rs8178847 | 6.8% | 8.0% | 0.010 | 0.809 | 4.6 | 0.97 |
| insulin receptor substrate-1 | IRS1 | rs4675096 | 6.4% | 8.0% | 0.010 | 0.545 | 4.7 | 0.97 |
| lipase A | LIPA | rs6586179 | 9.7% | 11.0% | 0.012 | 0.365 | −3.4 | 0.98 |
| retinoic acid receptor, beta | RARB | rs322695 | 10.2% | 23.0% | 0.033 | 0.639 | −3.3 | 1.00 |
| cholinergic receptor, muscarinic 3 | CHRM3 | rs7520974 | 46.6% | 47.0% | 0.034 | 0.801 | −1.9 | 1.00 |
| apolipoprotein A-IV | APOA4 | rs675 | 25.0% | 20.0% | 0.035 | 0.567 | −2.3 | 1.00 |
| Edema Markers | | | | | | | | |
| neuropeptide Y | NPY | rs1468271 | 3.4% | n/a | 0.248 | 0.006 | 0.4 | 0.88 |
| glycogen synthase 1 (muscle) | GYS1 | rs2287754 | 9.3% | 7.0% | 0.716 | 0.013 | 0.3 | 0.99 |
| chemokine (C-C motif) ligand 2 | CCL2 | rs3760396 | 15.9% | 26.0% | 0.285 | 0.015 | −0.2 | 0.99 |
| oxidized low density lipoprotein receptor 1 | OLR1 | rs2742115 | 28.4% | 27.0% | 0.360 | 0.015 | 0.2 | 1.00 |
| growth hormone releasing hormone | GHRH | rs6032470 | 15.9% | 16.0% | 0.960 | 0.023 | −0.2 | 1.00 |
| adrenergic, beta-1-, receptor | ADRB1 | rs2429511 | 44.3% | 40.0% | 0.068 | 0.033 | 0.1 | 1.00 |
| acetyl-Coenzyme A carboxylase beta | ACACB | rs34274 | 14.8% | 10.0% | 0.891 | 0.036 | −0.1 | 1.00 |
| scavenger receptor class B, member 2 | SCARB2 | rs894251 | 14.2% | 9.0% | 0.195 | 0.041 | 0.2 | 1.00 |
| histamine receptor H3 | HRH3 | rs1614845 | 15.3% | 22.0% | 0.932 | 0.042 | 0.1 | 1.00 |
| angiotensin I converting enzyme 1 | ACE | rs4333 | 46.6% | 49.0% | 0.757 | 0.044 | 0.1 | 1.00 |

TABLE 8

Allele frequencies, p-values, coefficients and FDR p-values of the top markers associated to HB1AC. Negative coefficients indicate protective marker status and positive, risk.

| | | | |
|---|---|---|---|
| HB1AC markers | | | |
| phosphoinositide-3-kinase, regulatory subunit 1 (p85 alpha) | PIK3R1 | rs10515070 | 0.706 |
| phosphoinositide-3-kinase, regulatory subunit 1 (p85 alpha) | PIK3R1 | rs706713 | 0.698 |
| acetyl-Coenzyme A carboxylase alpha | ACACA | rs8081866 | 0.499 |
| guanine nucleotide binding protein (G protein), alpha activating activity polypeptide O | GNAO1 | rs4784642 | −0.422 |
| endothelin 1 | EDN1 | rs5369 | −0.679 |
| insulin receptor | INSR | rs4804103 | 0.467 |
| lipase, hepatic | LIPC | rs6083 | 0.406 |
| glutamate decarboxylase 1 (brain, 67 kDa) | GAD1 | rs3791850 | 0.393 |
| brain-derived neurotrophic factor | BDNF | rs2049045 | −0.512 |
| brain-derived neurotrophic factor | BDNF | rs6265 | −0.5 |
| acetyl-Coenzyme A acetyltransferase 1 (acetoacetyl Coenzyme A thiolase) | ACAT1 | rs11212515 | −0.376 |
| acetyl-Coenzyme A acetyltransferase 1 (acetoacetyl Coenzyme A thiolase) | ACAT1 | rs10890819 | −0.376 |
| insulin receptor | INSR | rs891087 | 0.604 |
| Fms-related tyrosine kinase 1 (vascular endothelial growth factor/vascular permeability factor receptor) | HIF1A | rs2301108 | 0.532 |
| ATP-binding cassette, sub-family B (MDR/TAP), member 1 | ABCB1 | rs1128503 | −0.35 |
| uncoupling protein 2 (mitochondrial, proton carrier) | UCP2 | rs660339 | −0.357 |
| apolipoprotein B (including Ag(x) antigen) | APOB | rs1801701 | 0.692 |

Key:
SNP, single nucleotide polymorphism;
MAF, minor allele frequency;
CEU, persons of Northern and Western European ancestry;
BMI, body mass index;
EDM, edema;
Coeff, regression coefficient;
FDR, false discovery rate.

Example 2

Physiogenomic Comparison of BMI and Edema Profiles

The side effects BMI and edema for common and distinct SNP associations were compared. To illustrate how physiogenomics analysis discriminates between these phenotypes, FIG. 5 plots the comparative significance of SNP associations with edema (ordinate) and BMI (abscissa). Gene markers clustered in the sector at the origin are not significantly associated with either phenotype. Gene markers in the upper right quadrant convey risk. Those found in the uppermost shaded sector are risk factors for edema, whereas those in the rightmost shaded sector are risk factors for BMI. Gene markers in the lower left quadrant are protective. Those found in the lowermost shaded sector are protective for edema, whereas those in the leftmost shaded sector are protective for BMI. Markers adjoining the tips of the shaded sectors approximate significance for both edema and BMI. There were no markers protective for one phenotype and conveying risk for the other (upper left and lower right quadrants).

For example, ADORA1 gene strongly associates with BMI risk ($p<0.0003$) but not edema. The NPY gene strongly associates with edema risk ($p<0.006$) but not BMI. The LIPA gene associates with BMI protection only ($p<0.012$) and the CCL2 gene associates with edema protection only ($p<0.015$).

A striking aspect of the plot in is the aggregation of the markers toward "risk" or "protection" for either phenotype or both phenotypes. No marker was associated with risk for one phenotype and simultaneous protection for another. This pattern of polarity suggests that the phenotypes are linked to some extent possibly through interlocking physiological pathways.

In another representation, a physiogenomic contour of an efficacy phenotype, HbA1c, and two safety phenotypes, BMI and Edema, is shown in FIG. 6. The contour represents as circles the 20 genes with the most significant p-values to any of the three phenotypes. The position of each circle indicates the relative degree of association. Genes associated with only one particular response will be close to the corresponding vertex. The most significant BMI association is with ADORA1. The most significant HbA1c association is with PIK3R1. Uncoupling protein 2 (UCP2) is located between HbA1c and BMI, indicating that it plays a role in both responses. Indeed, UCP2 has a central role in energy balance, body weight, obesity, and thermoregulation. The most significant edema association is with NPY.

The contour shows that the three response phenotypes are associated with different genes, reflected in the three separate clusters of genes in FIG. 6. The HbA1c and BMI phenotypes may have some genetic factors in common, while the edema phenotype appears separate.

Previous physiological studies of thiazolidinediones have mostly used animal models. To our knowledge, the present report is the first to examine clinical response in humans as a source of mechanistic discovery. The results presented herein suggest that polymorphism in genes relevant to non-overlapping physiological pathways may affect the symptomatology of thiazolidinedione side effects. An association of BMI during thiazolidinedione therapy with polymorphisms in genes affecting adenosine, an adiponectin receptor, pyruvate kinase (muscle), and uncoupling protein 2. In contrast, edema induced by thiazolidinedione therapy is associated with polymorphisms in genes controlling vascular permeability. Consequently, it is possible that thiazolidinedione safety may require monitoring a constellation of independent syndromes with varying innate predispositions in the population and diverse physiological mechanisms encompassing various gene pathways.

A multi-gene model is developed where an individual's configuration of various significant SNPs can reliably predict the probability of thiazolidinedione-related adverse events for each patient. Generalized clinical use of such diagnostics for DNA-guided medical management could help improve thiazolidinedione tolerability and safety as these drugs are deployed ever more widely in treatment not only of diabetes but also of pre-diabetic conditions. The determination of individualized treatment most suitable to each patient, using his/her genome for clinical decision support, and the implementation of drug prescription safeguards, are integral to evidence-based medicine and personalized diabetic healthcare.

Recently, various meta analyses have suggested that rosiglitazone may increase the risk for myocardial infarction (MI) whereas pioglitazone does not. Reports on the MI risk have since been disputed. Still, many medical commentaries have emphasized the lack of cardiovascular benefit with rosiglitazone, suggested that the increased insulin sensitivity it induces may not be effective in reducing cardiovascular disease risk, and recommend caution in its use. The mechanism for the suggested increased cardiovascular risk in patients receiving rosiglitazone is unclear. Whether these effects are drug-specific or represent a class effect is also presently unknown, and likely masked by the concomitant statin therapy that is often required in diabetes patients.

Without being held to theory, it is hypothesized that several of the genes related to BMI through thiazolidinedione therapy also influence the risk for myocardial infarction. Several genes in the present study have known roles in thrombosis, ischemic responses, or other mechanisms predisposing to infarction. The strongest association with BMI in the data set is through ADORA1. Adenosine type A1 receptors participate in the protective effects of ischemic preconditioning through the initiation of the protective signal transduction cascade during reperfusion, mediated in part through the activation of protein kinase C. Thus adenosine receptor 1 agonists have tissue protective properties. With such evidence, it is possible to hypothesize that those ADOR1 gene variants that decrease gene expression may also raise the risk of myocardial infarction. Other genes with roles in the physiological response to ischemia include CHRM3 and UCP2. CHRM3 participates in the response to cerebral ischemia, and CHRM3 receptors have been identified in the myocardium. UCP2 expression increases the sensitivity of cardiac myocytes to hypoxia-reoxygenation. The protein expression of UCP2 may offer protection from cerebral ischemic injury through a cascade in which PPARgamma-mediated induction of UCP2 leads to neuroprotection. Further investigation of physiogenomic links between the risk of MI and these genes is warranted can be enhanced with attention to candidate genes already linked to BMI.

A "phenotype" is a trait or collection of traits that is/are observable in an individual or population. The trait can be quantitative or qualitative.

A "polymorphism" is a locus that is variable; that is, within a population, the nucleotide sequence at a polymorphism has more than one version or allele. One example of a polymorphism is a "single nucleotide polymorphism" (SNP), which is a polymorphism at a single nucleotide position in a genome (the nucleotide at the specified position varies between individuals or populations).

A "locus" is a chromosomal position or region. For example, a polymorphic locus is a position or region where a polymorphic nucleic acid, trait determinant, gene or marker is located. A "gene locus" is a specific chromosome location in the genome of a species where a specific gene can be found. A "marker" refers to a nucleotide sequence or encoded product thereof (e.g., a protein) used as a point of reference when identifying a locus or a linked locus. A marker can be derived from genomic nucleotide sequence or from expressed nucleotide sequences (e.g., from an RNA, a cDNA, etc.), or from an encoded polypeptide. The term also refers to nucleic acid sequences complementary to or flanking the marker sequences, such as nucleic acids used as probes or primer pairs capable of amplifying the marker sequence.

A "gene" is one or more sequence(s) of nucleotides (that is a polynucleotide) in a genome that together encode one or more expressed molecule, e.g., an RNA, or polypeptide. The gene can include coding sequences that are transcribed into RNA, which may then be translated into a polypeptide sequence, and can include associated structural or regulatory sequences that aid in replication or expression of the gene. Genes of interest herein include genomic sequences that encode, ADORA1, PKM2, ADIPOR2, UCP2, APOH, IRS1, LIPA, RARB, CHRM3, APOA4, NPY, GYS1, OLR1, ADRB1, SCARB2, HRH3, ACE, CCL2, GHRH, ACACB, PIK3R1, ACACA, GNAO1, EDN1, and INSR. All genes are given the standard nomenclature set forth by The Human Genome Organization (HUGO) as of April 2008.

A "set" of markers or probes refers to a collection or group of markers or probes, or the data derived therefrom, used for a common purpose, e.g., identifying an individual with a specified phenotype. Frequently, data corresponding to the markers or probes, or derived from their use, is stored in an electronic medium. While each of the members of a set possess utility with respect to the specified purpose, individual markers selected from the set as well as subsets including some, but not all of the markers, are also effective in achieving the specified purpose.

Genetic "linkage" occurs when particular genetic loci or alleles for genes are inherited jointly. The phrase "closely linked", in the present application, means that recombination between two linked loci (e.g., an SNP such as one identified herein and a second linked allele) occurs with a frequency of equal to or less than about 20%. Put another way, the closely (or "tightly") linked loci (e.g., SNPs) co-segregate at least 80% of the time. A linked locus is particularly useful when it is closely linked to a correlated polymorphism. Thus, in one embodiment, tightly linked loci such as a correlated locus and a second locus display an inter-locus recombination frequency of about 20% or less, e.g., 15% or less, e.g., 10% or less, specifically about 9%, 8%, 7%, 6%, 5%, 4%, 3% or 2% or less. In other embodiments, the loci display a recombination frequency of about 1%, 0.75%, 0.5%, 0.25% or 0.1% or less. Closely linked loci are also said to be "proximal to" each other. The term "haplotype" refers to a region of a chromosome that contains one or more polymorphic sites that tend to be inherited together (i.e., are in linkage disequilibrium). Combinations of polymorphic forms at the polymorphic sites within a block cosegregate in a population more frequently than combinations of polymorphic sites that occur in different haplotype blocks.

Haploypes can be determined using Haploview (of MIT Broad Institute) as tag SNPs for the haplotype block including the index SNP. All default settings are used for the haplotype block selection as well as the tag SNP selection. The CEU population genotypes are used. No attempt is made to limit the number, they range from 5 to 15. Tag SNPs are sorted in order of decreasing power, so if the number needs to be limited, some should be from the end of each list. The SNPs of each list will capture any other SNP in the haplotype block with an $r^2$ of 0.8 or better, including the index SNP. Haploview information: Haploview 4.1, 29 Apr. 2008. The haplotypes included herein were determined by this method.

A marker polymorphism or allele is "correlated" with a specified phenotype when it can be statistically linked (positively or negatively) to the phenotype.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A physiogenomics method for determining a human individual's protection from or risk for developing a body mass index increase associated with the use of a thiazolidinedione drug, comprising assaying genetic material from the human individual with Type 2 diabetes for the presence of a risk genetic marker and a protective genetic marker to produce a combinatorial genotype for the human individual, wherein the human individual with Type 2 diabetes is undergoing thiazolidinedione therapy or is an individual for whom thiazolidinedione therapy may be indicated, wherein the risk marker is rs903361 (ADORA1) (SEQ ID NO: 1) and the protective marker is rs6586179 (LIPA) (SEQ ID NO: 7); and determining the protection from or risk for developing a body mass index increase in the human individual in response to the use of a thiazolidinedione drug by comparing the combinatorial genotype for the human individual with a predictive model comprising phenotype and genotype data for a thiazolidinedione drug-treated population, wherein the phenotype data includes body mass index for the thiazolidinedione drug-treated population, and wherein the thiazolidinedione drug is used in the treatment of Type 2 diabetes, wherein a minor allele copy number at position 22 of SEQ ID NO: 1 is associated with a likelihood of a body mass index increase associated with the use of a thiazolidinedione drug in the human individual and the a minor allele copy number at position 22 of SEQ ID NO: 7 is associated with a likelihood of a body mass index decrease associated with the use of a thiazolidinedione drug in the human individual.

2. The method of claim 1, wherein the predictive model includes age as a covariate.

3. The method of claim 1, further comprising administering a strict diet to the individual at risk for developing a body mass index increase in the human individual in response to the use of a thiazolidinedione drug.

4. The method of claim 1, further comprising administering a low dose of thiazolidinedione drug to the individual at risk for developing a body mass index increase in response to the use of a thiazolidinedione drug.

5. The method of claim 1, further comprising implementing a switch to a different class of drugs to the individuals at risk for developing a body mass index increase in response to the use of a thiazolidinedione drug.

6. The method of claim 1, further comprising monitoring side effects of thiazolidinedione drug and implementing prophylactic treatment to the individuals at risk for developing a body mass index increase in response to the use of a thiazolidinedione drug.

7. The method of claim 1, wherein the predictive model is in the form of a table, algorithm, nomogram, a web-based portal, or a downloadable guidance that includes correlations between the minor allele copy numbers at position 22 of SEQ ID NO: 1 and position 22 of SEQ ID NO:7 and the risk of body mass index decrease associated with the use of a thiazolidinedione drug in the human individual.

* * * * *

SEQUENCE LISTING

```
<160> NUMBER OF SEQ ID NOS: 37

<210> SEQ ID NO 1
<211> LENGTH: 42
<212> TYPE: DNA
<213> ORGANISM: Homo sapiens
<220> FEATURE:
```

-continued

```
<221> NAME/KEY: misc_feature
<222> LOCATION: (22)..(22)
<223> OTHER INFORMATION: r = a or g

<400> SEQUENCE: 1
agtggtcagg cttcacccag trctacagag cagatctggg ac          42

<210> SEQ ID NO 2
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 2
caggctcagg gtctaaattc crtatccttt cttccatacc ct          42

<210> SEQ ID NO 3
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 3
cttttcacag gaaaatttct trggagtcta ttgtcactgt ct          42

<210> SEQ ID NO 4
<211> LENGTH: 42
<212> TYPE: DNA
<213> ORGANISM: Homo sapiens
<220> FEATURE:
<221> NAME/KEY: misc_feature
<222> LOCATION: (22)..(22)
<223> OTHER INFORMATION: r = a or g

<400> SEQUENCE: 4
acaccgcggt actgggcgct grctgtagcg cgcactggcc cc          42

<210> SEQ ID NO 5
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: r = a or g

<400> SEQUENCE: 5
tacctacgtt tgcaacactt crtgtttata agccatcagc tg          42

<210> SEQ ID NO 6
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: r = a or g

<400> SEQUENCE: 6
agtgttttcc aaggtgtgat traaaatgga gatttcttac ct          42

<210> SEQ ID NO 7
```

```
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: r = a or g

<400> SEQUENCE: 7
accctgcatt ctgaggggtc trgagggaaa ctgacagctg tg                              42

<210> SEQ ID NO 8
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: r = a or g

<400> SEQUENCE: 8
cctgtaggat tgtgttcctc traaactgtc ccctaaatta tg                              42

<210> SEQ ID NO 9
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: r = a or g

<400> SEQUENCE: 9
cagctgaaag aaagacaaat artagatacc cactgcatgg ct                              42

<210> SEQ ID NO 10
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: w = a or t

<400> SEQUENCE: 10
gagaaagaga gccaggacaa gwctctctcc ctccctgagc tg                              42

<210> SEQ ID NO 11
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: r = a or g

<400> SEQUENCE: 11
gaccctgtaa ttttcagaaa crcacatagg agtgggtgtc tg                              42

<210> SEQ ID NO 12
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: r = a or g

<400> SEQUENCE: 12
```

```
cgggaagctt gcaagacgct crgcttccta ttgcaagacc gc                              42
```

<210> SEQ ID NO 13
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: r = a or g

<400> SEQUENCE: 13

```
acatgtgtac acgtggtgta trttaaaaac ttcaggctct ct                              42
```

<210> SEQ ID NO 14
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: r = a or g

<400> SEQUENCE: 14

```
tcctggcttc cttctggacc crcaaggggc agtctcaaaa ta                              42
```

<210> SEQ ID NO 15
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: r = a or g

<400> SEQUENCE: 15

```
ctcaggaggc cttactgtgc crtggttctt gccctttgat tt                              42
```

<210> SEQ ID NO 16
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: r = a or g

<400> SEQUENCE: 16

```
aagctgctgt aaatggaggc trcctagaga ggagagggcc tg                              42
```

<210> SEQ ID NO 17
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: r = a or g

<400> SEQUENCE: 17

```
ctgaccccaa gagcgagggg arcccaactc tgtgctctca cc                              42
```

<210> SEQ ID NO 18
<211> LENGTH: 42
<212> TYPE: DNA
<213> ORGANISM: homo sapiens
<220> FEATURE:
<221> NAME/KEY: misc_feature
<222> LOCATION: (22)..(22)

<223> OTHER INFORMATION: s = c or g

<400> SEQUENCE: 18
gacagagaga ggacccaagc asgcaactag ttggaggact tg        42

<210> SEQ ID NO 19
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: r = a or g

<400> SEQUENCE: 19
agccccagtc cttaccggaa crgtagaggc ttaacaaaca tt        42

<210> SEQ ID NO 20
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: r = a or g

<400> SEQUENCE: 20
ctctatgatt tcacagtgat grgctcaagt atgtgtctgc tt        42

<210> SEQ ID NO 21
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: r = a or g

<400> SEQUENCE: 21
tttccttcca atatattcta crtaagttcc cggaaagtcc cc        42

<210> SEQ ID NO 22
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: w = a or t

<400> SEQUENCE: 22
agattcctcc ctgtacgata gwgtcttact tttccacttt gc        42

<210> SEQ ID NO 23
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: r = a or g

<400> SEQUENCE: 23
gagaagctcc catctagctg trtatgatag ggggtttatc tg        42

<210> SEQ ID NO 24
<211> LENGTH: 42
<212> TYPE: DNA

```
<213> ORGANISM: homo sapiens
<220> FEATURE:
<221> NAME/KEY: misc_feature
<222> LOCATION: (22)..(22)
<223> OTHER INFORMATION: r = a or g

<400> SEQUENCE: 24
attttcttct gggtggccct aractgcttt cttttccccc at                              42

<210> SEQ ID NO 25
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: r = a or g

<400> SEQUENCE: 25
cacaaaggca acagaccgtg araatagatg ccaatgtgct ag                              42

<210> SEQ ID NO 26
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: r = a or g

<400> SEQUENCE: 26
tcctgtgaga gagttgagag crataatttt agggtggtta tt                              42

<210> SEQ ID NO 27
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: r = a or g

<400> SEQUENCE: 27
gtctttctcc agatgatgcc arttttgtgg atgccattca ta                              42

<210> SEQ ID NO 28
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: r = a or g

<400> SEQUENCE: 28
cacaacaagg gtttagctct arggagagca gaggcaggat ga                              42

<210> SEQ ID NO 29
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: s = c or g

<400> SEQUENCE: 29
aaatctctct tcttcgataa asttcccagg aggtaaccca at                              42
```

```
<210> SEQ ID NO 30
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: r = a or g

<400> SEQUENCE: 30
ttggctgaca ctttcgaaca crtgatagaa gagctgttgg at                             42

<210> SEQ ID NO 31
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: w = a or t

<400> SEQUENCE: 31
ggattgcaat aaagggaagg awgaaggatg attttggctt ga                             42

<210> SEQ ID NO 32
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: r = a or g

<400> SEQUENCE: 32
accagaagct agcataatgg artatcgccc ctcactttgt tc                             42

<210> SEQ ID NO 33
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: r = a or g

<400> SEQUENCE: 33
gcaggtctcc acacacctgc crtccaggta gaagttgcgg ca                             42

<210> SEQ ID NO 34
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: r = a or g

<400> SEQUENCE: 34
ctactggaag attagccacg trttgagttt tgtctttgca tt                             42

<210> SEQ ID NO 35
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: r = a or g
<220> FEATURE:
```

-continued

```
<221> NAME/KEY: misc_feature
<222> LOCATION: (37)..(37)
<223> OTHER INFORMATION: n is a, c, g, or t

<400> SEQUENCE: 35
actctgcacc ttcaggttca grcccttcaa gatctancag ga                          42

<210> SEQ ID NO 36
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: r = a or g

<400> SEQUENCE: 36
acaccgcggt actgggcgct grctgtagcg cgcactggcc cc                          42

<210> SEQ ID NO 37
<211> LENGTH: 42
<212> TYPE: DNA
<213> ORGANISM: homo sapiens
<220> FEATURE:
<221> NAME/KEY: misc_feature
<222> LOCATION: (22)..(22)
<223> OTHER INFORMATION: r = a or g

<400> SEQUENCE: 37
tcagatggaa aaatgaagtc crgattcatt ctgggtcttt cc                          42
```